United States Patent
Diaz

[19]

[11] Patent Number: 5,814,065
[45] Date of Patent: Sep. 29, 1998

[54] SUTURE DELIVERY TOOL

[75] Inventor: Roberto Diaz, Miami, Fla.

[73] Assignee: Cordis Corporation, Miami Lakes, Fla.

[21] Appl. No.: 599,063

[22] Filed: Feb. 9, 1996

[51] Int. Cl.[6] .................................................. A61B 17/04
[52] U.S. Cl. ...................... 606/213; 606/145; 606/139; 606/148; 112/169
[58] Field of Search ..................... 606/158, 148, 606/150, 139, 145, 144; 112/169, 180.03; 604/174, 175, 177, 178, 106, 107

[56] References Cited

U.S. PATENT DOCUMENTS

| | | |
|---|---|---|
| 4,587,969 | 5/1986 | Gillis . |
| 4,744,364 | 5/1988 | Kensey . |
| 4,852,568 | 8/1989 | Kensey . |
| 4,890,612 | 1/1990 | Kensey . |
| 4,929,246 | 5/1990 | Sinofsky . |
| 5,021,059 | 6/1991 | Kensey et al. . |
| 5,041,129 | 8/1991 | Hayhurst et al. . |
| 5,053,046 | 10/1991 | Janese . |
| 5,061,274 | 10/1991 | Kensey . |
| 5,088,979 | 2/1992 | Filipi et al. . |
| 5,108,421 | 4/1992 | Fowler . |
| 5,129,882 | 7/1992 | Weldon et al. . |
| 5,149,331 | 9/1992 | Ferdman et al. . |
| 5,203,787 | 4/1993 | Noblitt et al. . |
| 5,221,259 | 6/1993 | Weldon et al. . |
| 5,222,974 | 6/1993 | Kensey et al. . |
| 5,226,876 | 7/1993 | Filipi et al. . |
| 5,292,332 | 3/1994 | Lee . |
| 5,320,632 | 6/1994 | Heidmueller ............................ 606/144 |
| 5,364,408 | 11/1994 | Gordon .................................. 606/144 |
| 5,368,601 | 11/1994 | Sauer et al. ............................ 606/144 |
| 5,374,275 | 12/1994 | Bradley et al. ......................... 606/144 |
| 5,403,329 | 4/1995 | Hinchcliffe ............................. 606/147 |
| 5,413,571 | 5/1995 | Katsaros et al. . |
| 5,417,699 | 5/1995 | Klein et al. ............................. 606/144 |
| 5,419,777 | 5/1995 | Hofling .................................. 604/264 |
| 5,437,292 | 8/1995 | Kipshidze et al. . |
| 5,443,481 | 8/1995 | Lee . |
| 5,496,332 | 3/1996 | Sierra et al. ............................ 606/139 |
| 5,509,900 | 4/1996 | Kirkman ................................ 604/104 |
| 5,527,322 | 6/1996 | Klein et al. ............................. 606/144 |
| 5,540,715 | 7/1996 | Katsaros et al. . |
| 5,562,688 | 10/1996 | Riza ....................................... 606/148 |
| 5,613,974 | 3/1997 | Andreas et al. . |
| 5,653,718 | 8/1997 | Yoon ..................................... 606/148 |

FOREIGN PATENT DOCUMENTS

| | | |
|---|---|---|
| 0 482 350 A2 | 4/1992 | European Pat. Off. . |
| WO 92/22252 | 12/1992 | WIPO . |
| 95/05121 | 2/1995 | WIPO . |

OTHER PUBLICATIONS

European Search Report for Application No. 97300784.2, three pages.
Three page brochure of Raychem Corporation Medical Products on Tinel Alloy BB Superalastic Alloy, date unknown.
Four page brochure of Raychem Corporation Medical Products on Tinel Alloy BC–SE Superalastic Alloy, date unknown.
Five page brochure of Raychem Corporation Medical Products on Tinel Superalastic Alloys, dated Feb., 1993.
Four page Perclose, Inc. Catalog dated no later than 1993.

*Primary Examiner*—Michael Powell Buiz
*Assistant Examiner*—Tina T. D. Pham
*Attorney, Agent, or Firm*—Watts, Hoffmann, Fisher & Heinke Co. L.P.A.

[57] ABSTRACT

An apparatus for closing a wound in a vessel wall of a patient includes an elongated member having a proximal end portion and a distal end portion spaced from the proximal end portion in a longitudinal direction. First needle lumens extend in the elongated member between the proximal end portion and the distal end portion. A tip is disposed near the distal end portion of the elongated member and includes second needle lumen portions aligned with the first needle lumens. The tip is spaced apart from the elongated member in the longitudinal direction to form a recess between the tip and the elongated member for receiving the vessel wall.

18 Claims, 5 Drawing Sheets

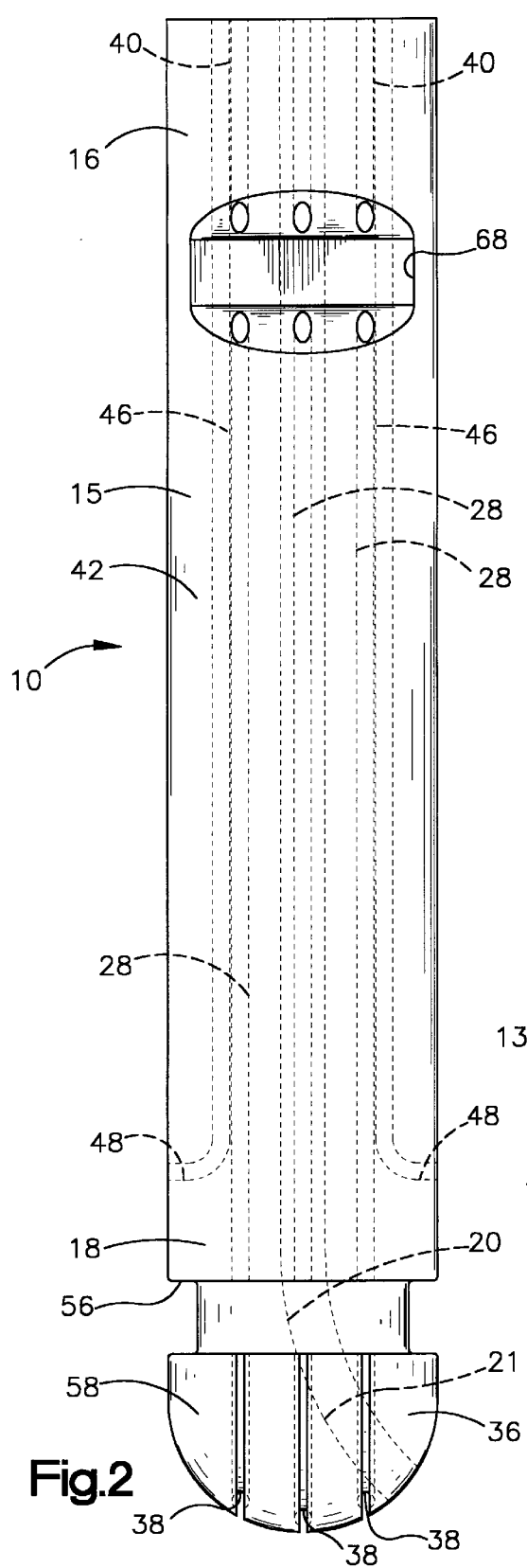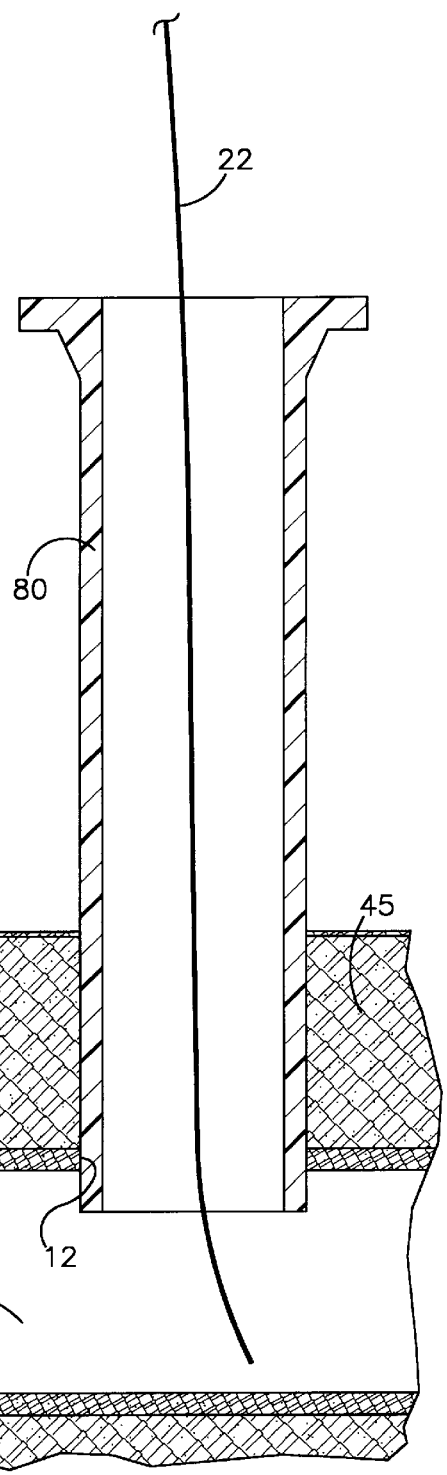
Fig.2
Fig.3

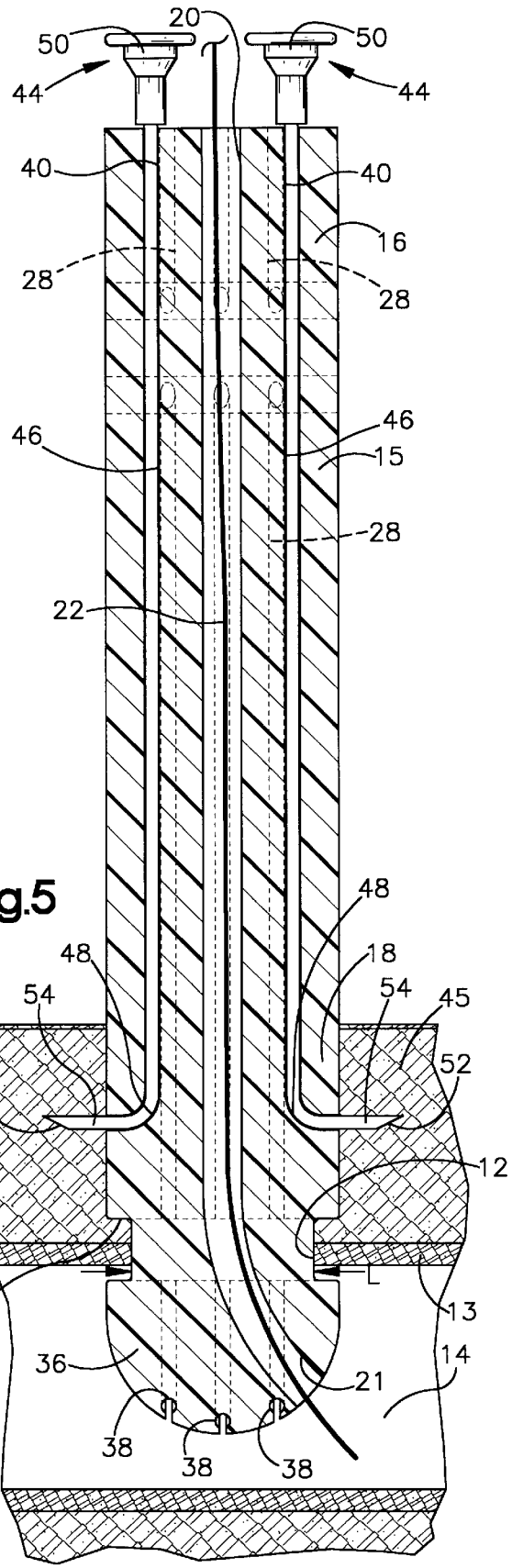

SUTURE DELIVERY TOOL

TECHNICAL FIELD

The present invention relates to a surgical instrument and to a method of its use, and more specifically, to a suture delivery tool for closing a surgical incision or wound in the vessel wall of a patient.

BACKGROUND OF THE INVENTION

Some medical procedures require surgical access into the vascular system of a patient through an artery or other vessel to accommodate a catheter sheath introducer or dilator for the insertion of instruments for therapeutic and diagnostic procedures. Medical instruments such as guidewires, catheters, balloon angioplasty devices and the like are typically inserted into the vascular system through a catheter sheath introducer having its distal end extending into the vessel. Once in the vascular system, the instruments can be moved to the area requiring the medical procedure.

A catheter sheath introducer has a relatively large outer diameter that leaves a wound having a corresponding size in the vessel wall. After the medical procedure has been completed, the wound from the catheter sheath introducer must be closed as soon as possible to stop bleeding from the vessel. One common technique to stop the bleeding is the application of continuous pressure to the wound until the patient's blood clots sufficiently to seal the vessel. One drawback to such a technique is that it requires medical personnel to dedicate about an hour of time. Moreover, serious bleeding complications, such as a hematoma, can occur due to the clotting process. Patients may thus be required to spend at least one night in the hospital for rest and observation. This hospital stay is an inconvenience for the patient and increases the cost of the medical procedure.

Instruments may be used instead of the direct pressure technique for closing wounds in vessels of the patient. Such instruments typically insert a plug-like object or a clotting agent into the area of the wound to seal the vessel. The plug or clotting agent may be positioned either inside or outside the vessel and in close proximity to the outer vessel wall. Other plugs are placed directly in the vessel and secured against the inner vessel wall by an external suture extending into the wound and attached to the plug. Other devices dispense a foam, powder or gel into the wound area.

The use of plugs and clotting agents creates problems because the plugs or clotting agents may be unintentionally disposed in the vessel. In addition, the plug may slip into the vessel due to the application of external pressure to the wound. When the plugs and clotting agents protrude into the vessel they can partially occlude blood flow through the vessel at the site of the original wound, which may lead to thrombosis or stenosis.

Sutures have proven to be effective in closing and sealing surgical wounds. However, the prior art has failed to provide an instrument that uses sutures to close a relatively large wound, such as a wound from a catheter sheath introducer, easily and efficiently.

SUMMARY OF THE INVENTION

The present invention relates to a suture delivery tool and method of using the suture delivery tool for closing a relatively large wound in a vessel wall of a patient. The present invention does not suffer from the drawbacks associated with the direct pressure technique and the use of clotting agents and plugs.

An apparatus for closing a wound in a vessel wall of a patient in accordance with the invention includes an elongated member having a proximal end portion and a distal end portion spaced from the proximal end portion in a longitudinal direction. First needle lumens extend in the elongated member between the proximal end portion and the distal end portion. A tip is disposed near the distal end portion of the elongated member and includes second needle lumen portions aligned with the first needle lumens. The tip is spaced apart from the elongated member in the longitudinal direction to form a recess between the tip and the elongated member for receiving the vessel wall.

A preferred embodiment of the invention includes a central guidewire lumen extending between the proximal end portion and the distal end portion for receiving a guidewire. First and second groups of at least three needle lumens extend in the elongated member between the proximal end portion and the distal end portion. Hollow needle members are adapted to be received in the needle lumens and the needle lumen portions. The needle members and the second needle lumen portions form suture paths. First and second needle sets each have at least three hollow needle members.

At least two locker needle lumens extend between the proximal and distal end portions and are adapted to communicate with an exterior surface of the elongated member. Two locker needles are each adapted to be disposed in an associated one of the locker needle lumens.

More specifically, the elongated member and the tip have an oblong cross-sectional shape in a transverse plane extending perpendicular to the longitudinal direction. The second needle lumen portions are substantially U-shaped and communicate with an exterior surface of the tip along their entire lengths. At least three sutures are used, each of which can be connected to an associated suture advancing member.

When catheter sheath introducers of French size 8 are used, a minimum of two sutures is required to close the wound in the vessel. When catheter sheath introducers having French sizes of 11 and 12 are used (about 3.7 to 4 mm in diameter), at least three sutures are required. Four sutures could also be used. The catheter sheath introducer size approximates the size of the wound in the vessel. The wound may be somewhat larger than the sheath size due to tearing caused by the catheter sheath introducer.

The present invention is advantageous in that it easily and efficiently seals the wound in the vessel by simultaneously puncturing at least three holes in each side of the wound through which the sutures are passed. Due to the oblong cross-sectional transverse shape of the elongated member, the sutures may be placed preferably within 1 mm or less from the wound. This 1 mm spacing is important for quickly closing large wounds in the vessel. Because the needle members are preferably interconnected into sets of at least three needle members, interaction with the vessel is reduced, thereby increasing the efficiency and effectiveness of the procedure.

A method of the present invention generally includes inserting the distal end portion of the elongated member into a wound in the vessel wall of a patient. The vessel wall is punctured by inserting at least one hollow needle member into at least one first needle lumen of the elongated member on one side of the wound and by inserting at least one hollow needle member into at least one first needle lumen of the elongated member on another side of the wound. The needle member on one side of the wound and the needle member on the other side of the wound are both moved into an associated second needle lumen portion in the tip. The sutures are passed through the needle members and the second needle lumen portion in the tip. The elongated member is removed from the wound in the vessel and the wound is closed with the sutures.

A preferred method of the invention includes guiding the distal end portion of the elongated member to the wound by sliding the elongated member over the guidewire in the longitudinal direction. The first needle set is inserted into the needle lumens and through the vessel wall at one side of the wound. The second needle set is inserted into the needle lumens and through the vessel wall on the other side of the wound. The needle members of the first and second sets are moved into the needle lumen portions in the tip. The sutures are passed into the elongated member through the suture paths, i.e., through the first set of needle members, into associated needle lumen portions in the tip, and out the elongated member through the second set of needle members. The elongated member and guidewire are removed from the vessel and the sutures are tied to close the wound. The sutures are removed from the needle lumen portions of the tip while the sutures are disposed in the first and second sets of needle members.

More specifically, the locker needle members are inserted into the locker needle lumens into tissue near the vessel to lock the elongated member in position. The vessel wall is positioned in the recess between the elongated member and the tip by inserting the elongated member into the vessel with one set of needle members disposed in the first needle lumens. When blood flows from the first needle lumens without needles, the elongated member is withdrawn to a position where the blood flow from these first needle lumens stops. This process is repeated as necessary until the vessel wall is positioned within the recess.

Other embodiments of the invention are contemplated to provide particular features and structural variants of the basic elements. The specific embodiments referred to as well as possible variations and the various features and advantages of the invention will become better understood from the detailed description that follows, together in connection with the accompanying drawings.

BRIEF DESCRIPTION OF THE DRAWINGS

FIG. 2 is a front elevational view of the suture delivery tool;

FIG. 3 is a cross-sectional view of a catheter sheath introducer positioned along a guidewire in a vessel wall of a patient;

FIG. 4 is a cross-sectional view showing the suture delivery tool being moved to position the vessel wall in a recess near a tip of the tool;

FIG. 5 is a cross-sectional view of the suture delivery tool locked in the tissue, the tool being shown rotated 90° from the view shown in FIG. 4;

DETAILED DESCRIPTION OF PREFERRED EMBODIMENTS

Figure 1:
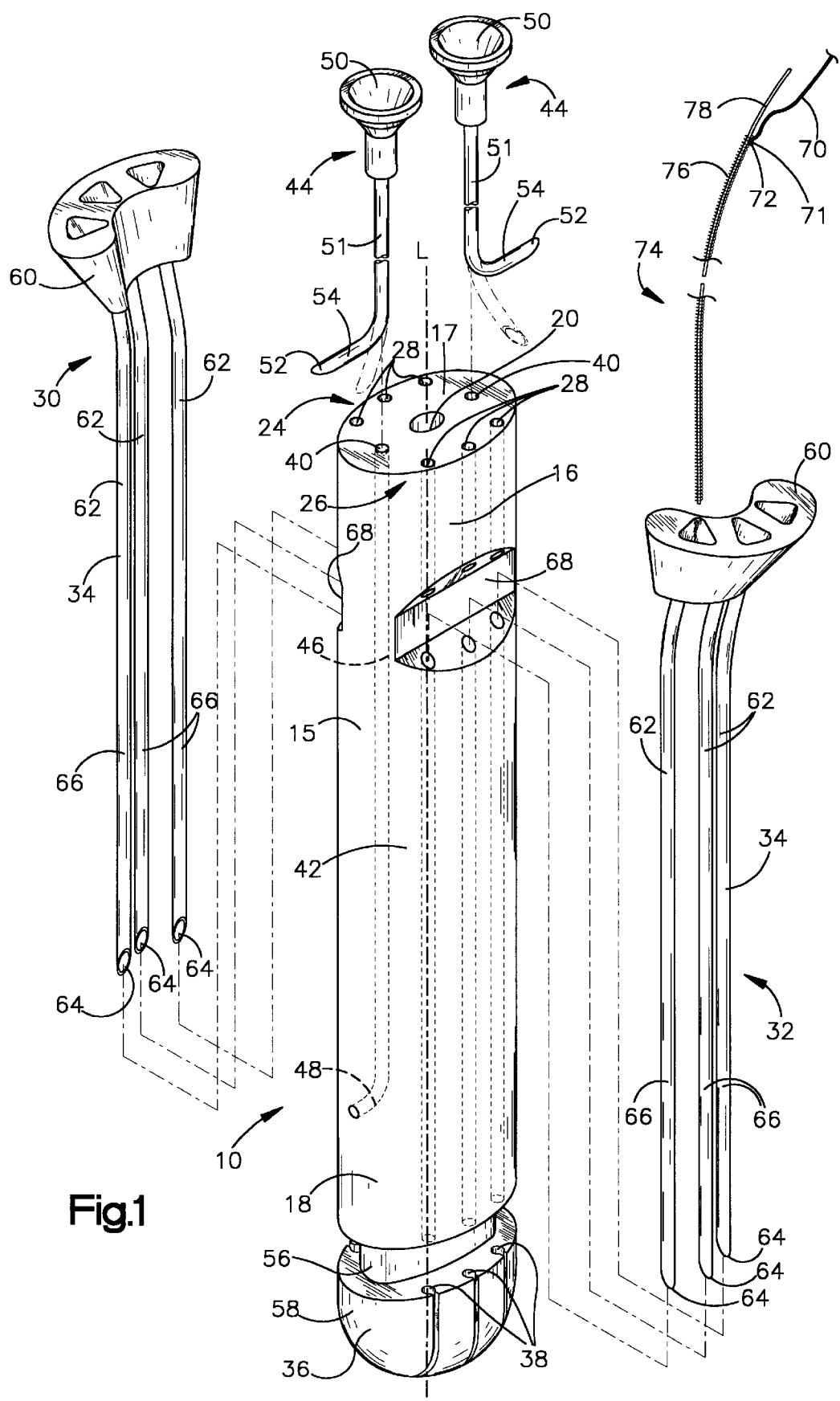
FIG. 1 is an exploded perspective view of a suture delivery tool constructed in accordance with the present invention.

Turning now to the drawings, FIGS. 1–3 show a suture delivery tool or apparatus 10 for closing a wound 12 such as in a wall 13 of a blood vessel 14. The wound 12 is typically caused by insertion of a catheter sheath introducer into the vessel 14. The apparatus 10 includes an elongated member 15 having a proximal end portion 16 with a proximal face 17 and a distal end portion 18 spaced from the proximal end portion 16 in a longitudinal direction L. A central guidewire lumen 20 extends between the proximal and distal end portions 16, 18 for receiving a guidewire 22. First and second needle lumen groups 24, 26 each have at least three first needle lumens 28 extending in the elongated member 15 between the proximal and the distal end portions 16, 18. The needle lumen groups 24, 26 receive first and second sets 30, 32 of needle members 34. A tip 36 is disposed near the distal end portion 18 of the elongated member 15 and includes second needle lumen portions 38 aligned with the first needle lumens 28 in a transverse plane perpendicular to the longitudinal direction L, as best shown in FIG. 1. At least two locker needle lumens 40 extend in the elongated member 15 between the proximal and distal end portions 16, 18 and communicate with an exterior surface 42 of the elongated member 15. Two locker needles 44 are each disposed in an associated one of the locker needle lumens 40 for insertion into tissue 45.

The three needle lumens 28 of the first lumen group 24 are radially spaced from the guidewire lumen 20 on one side of the elongated member 15. The three needle lumens 28 of the second lumen group 26 are radially spaced from the guidewire lumen 20 on the other side of the elongated member 15. The locker needle lumens 40 are radially spaced from the guidewire lumen 20 at opposite ends of the elongated member 15.

The first needle lumens 28 are preferably symmetrically radially arranged in the elongated member 15. That is, the first lumen group 24 is preferably a mirror image of the second lumen group 26 in top plan view with respect to a vertical plane bisecting the locker needle lumens 40 and extending in the longitudinal direction L. The elongated member 15 is oriented such that the wound 12 preferably extends along the vertical plane substantially in a direction of a length of the wound 12. The need lumens 28 are preferably arranged so that they will be located not greater than 1 mm from the side edges of the wound 12.

Distal end portions 54 of the locker needles 44 are each bent to extend at an angle less than 90°, more specifically, 50°–70°, from the straight portions 51. The magnitude of this angle may be changed, for example, by adjusting the diameter of the locker needles 44 and the radius of the bent lumen portions 48. The guidewire lumen 20 has a portion 21 (FIG. 2) that preferably extends at an angle of about 45° from the longitudinal direction L at the distal end portion 18. The guidewire 22 typically has a 0.018 inch diameter and a length of 14, 15 or 38 inches, for example.

The elongated member 15 preferably has an oblong cross-sectional shape as viewed perpendicular to the transverse plane (i.e., a top plan view), as shown by the proximal face 17 in FIG. 1. The elongated member 15 may have other cross-sectional shapes such as a circular one, as long as the needle members 34 are preferably not greater than 1 mm from the sides of the wound 12.

Each of the locker needle lumens 40 has a straight lumen portion 46 extending from the proximal end portion 16 toward the distal end portion 18 in a direction generally parallel to the longitudinal direction L. Each of the locker needle lumens 40 preferably includes an angled lumen portion 48 leading to the exterior surface 42 of the elongated member 15. The angled locker needle lumen portions 48 each extend at an angle less than 90°0 from the straight lumen portions 46, toward the proximal face 17. The angled lumen portions 48 correspond to the angle of the bend in the distal end portions 54 of the locker needles 44.

Each of the locker needles 44 includes a gripping portion 50, a straight portion 51 and a sharp point 52 at the distal end portion 54. The locker needles 44 are preferably formed of a "shape-memory" metal that permits the locker needles 44 to return to an original shape after being mechanically deformed. One example of a preferred "shape-memory" metal for the locker needles 44 is a nickel-titanium alloy such as Tinel™ Alloy BB by Raychem Corporation.

The locker needles 44 are originally formed with the distal end portion 54 being bent. The distal end portions 54 are mechanically straightened and inserted into their associated locker needle lumens 40. Once the elongated member 15, and hence the locker needles 44, are inserted into the human body the locker needles 44 and the distal end portions 54 resume their original bent shape. The bent distal end portions 54 of the locker needles 44 extend into their associated angled locker needle lumen portions 48 and into the tissue to inhibit movement of the elongated member 15 in the longitudinal direction, thereby locking the elongated member 15 in place.

The tip 36 is preferably integrally formed with the elongated member 15 but may also be formed as a separate member and then connected to the elongated member 15 in a manner known to those skilled in the art. The tip 36 is spaced apart from the elongated member 15 in the longitudinal direction L to form a recess 56 between the tip 36 and the elongated member 15. The recess 56 extends around the entire periphery of the elongated member 15, and the vessel wall 13 is received within the recess 56. The needle lumen portions 38 of the tip 36 are substantially U-shaped and open at their outer portions to communicate with an exterior surface 58 of the tip 36 along their entire lengths.

Three needles 34 of the first needle set 30 are inserted into the first lumen group 24 and three needles 34 of the second needle set 32 are inserted into the second lumen group 26. Four needles 34 may be used in each of the needle sets 30, 32, in which case four needle lumens are used in each of the needle lumen groups 24, 26. The needles 34 preferably have a grip member 60 at a proximal end portion 62 that interconnects the needles of each set 30, 32. The needles 34 have sharp points 64 at their distal end portions 66. Each of the needles 34 is preferably bent at its proximal end portion 62 so that the associated needle grip portion 60 is received by an associated opening 68 in the proximal end portion 16 of the elongated member 15. The needles 34 preferably have an outer diameter ranging from 0.018–0.027 inches and an inner diameter ranging from 0.010–0.018 inches.

At least three suture paths P are formed when the needles 34 are inserted into the first needle lumens 28. When the needles 34 are inserted into their corresponding first needle lumens 28, the second needle lumen portions 38 comprise lower portions of the suture paths P. Each of the lower portions interconnects the hollow interior of each needle 34 of the first needle set 30 with an associated hollow interior of a needle 34 of the second needle set 32 to form a suture path P. One half of a suture path P is shown by dotted lines in FIG. 6, the other half being omitted for clarity. When the needle member sets 30, 32 are inserted into the second needle lumen portions 38, the suture paths P extend from the proximal face 17 of the elongated member 15 through the hollow interior portions of the needles 34 of the first needle set 30, through the associated needle lumen portions 38, and through the hollow interior portions of the needles 34 of the second needle set 32 back to the proximal face 17. Each of the needles 34 in the first needle set 30 is disposed along the same suture path P as an associated one of the needles 34 in the second needle set 32.

The elongated member 15, the tip 36, and the gripping portions 50, 60 are formed of any suitable material known to those skilled in the art having properties including sufficient stiffness. For example, the elongated member 15 and the tip 36 may be formed of a biocompatible polymeric material such as polyurethane. These components may be fabricated by any conventional processing technique known to those skilled in the art, such as injection molding.

The sutures 70 are preferably made of a polypropylene monofilament known to those skilled in the art and are, for example, about 0.003 inches in diameter. Three of the sutures 70 are each connected at one of their ends 71 to an end portion 72 of an associated suture advancing or coil member 74. The sutures 70 are guided along the suture paths P by an associated one of the coil members 74. Each coil member 74 includes a helical coil 76 wrapped around a wire 78. The coil 76 is preferably made of high tensile stainless steel, for example, 0.0025 inches in diameter. The wire 78 is preferably made of stainless steel, for example, 0.010 inches in diameter. It will be appreciated by those skilled in the art that the coil 76, the wire 78 and the sutures 70 may be made from any suitable materials known to those skilled in the art and may have different dimensions.

In operation, a catheter sheath introducer 80 shown in FIG. 3, which was previously used during a medical procedure to introduce catheters or the like into the vascular system of the patient, is removed from the surgical wound 12 in the vessel wall 13. The guidewire 22 is left in the vessel 14. The width W of the wound 12 is depicted in FIG. 4 and the length L of the wound 12 is depicted in FIG. 5. However, the size and shape of the wound 12 are theoretical approximations, since the actual size and shape of the wound 12 in a living patient has not yet been able to be determined. The elongated member 15 is guided to the wound 12 by sliding elongated member 15 over the guidewire 22, the guidewire 22 being received by the guidewire lumen 20.

FIG. 4 shows how the elongated member 15 is disposed in the vessel 14 to position the vessel wall 13 in the recess 56. The needles 34 of the first set 30 are inserted into the associated first group 24 of the needle lumens 28. The second set of needles 32 is not yet inserted into the second group 26 of the needle lumens 28. The tip 36 is inserted through the wound 12 into the vessel 14 until blood spurts out the needle lumens 28 of the second needle lumen group 26. This indicates that the recess 56 has entered the vessel 14, since blood enters the needle lumens 28 of the second needle lumen group 26 through the recess 56. The elongated member 15 is then backed out of the vessel 14 until the bleeding through the second lumen group 26 stops, indicating that the recess 56 is just outside the vessel wall 13. This process is repeated as many times as necessary until medical personnel have determined the position of the elongated member 15 in the longitudinal direction L at which the vessel wall 13 is located in the recess 56, as shown in FIG. 5.

The locker needles 44 are inserted into their respective locker needle lumens 40 so that their bent distal portions 54 enter the tissue 45. This inhibits movement of the elongated member 15 in the longitudinal direction L, thereby locking the elongated member in place in the tissue 45.

Figures 6, 7:
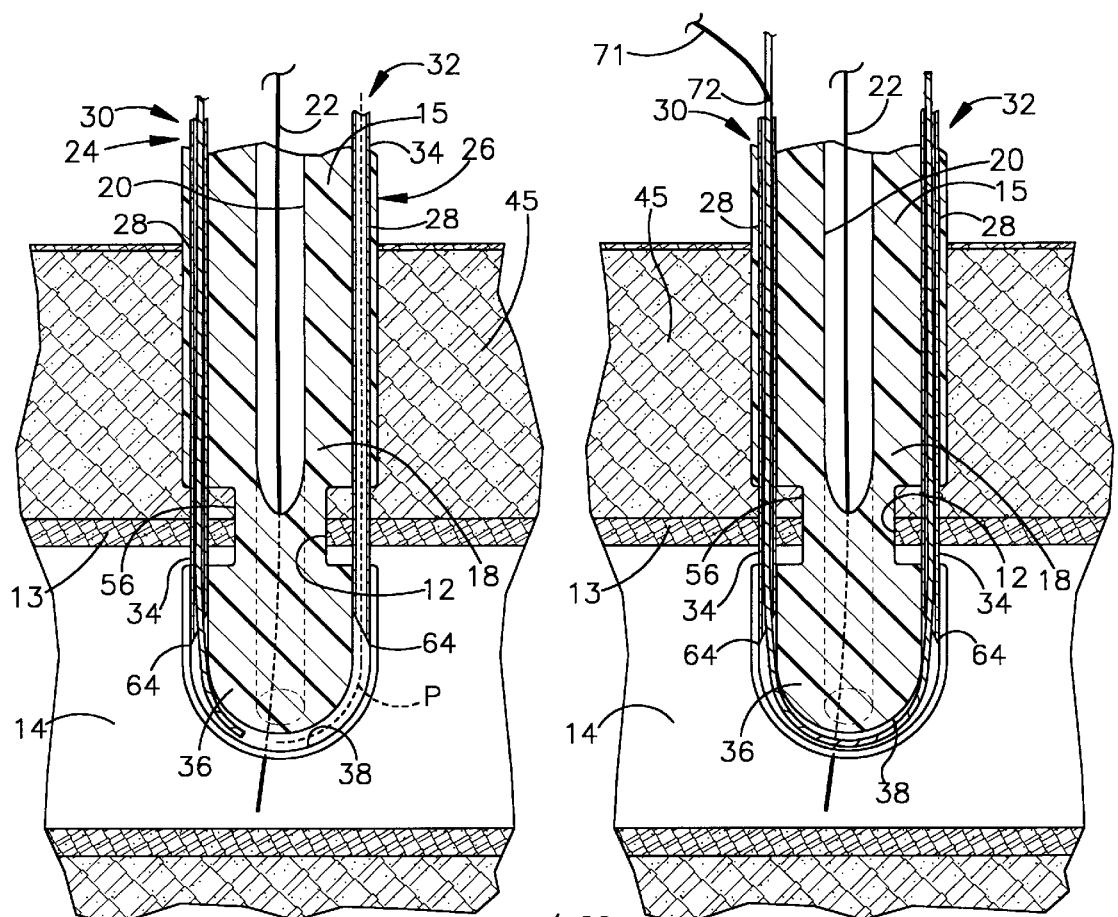
FIG. 6 is a cross-sectional view of the suture delivery tool rotated as in FIG. 4, showing a suture advancing member moved through a needle member of a first set of needle members and into the tip.
FIG. 7 is a cross-sectional view showing the suture advancing member moved through an associated needle member of a second set of needle members.

As shown in FIG. 6, the first set of needles 30 is inserted into the first group of needle lumens 24 to pierce the vessel wall 13 on one side of the wound 12. The second set of needles 32 is inserted into the second group of needle lumens 26 to pierce the vessel wall 13 on the other side of the wound 12.

The needles 34 of the first and second needle sets 30, 32 are moved into their associated needle lumen portions 38 in the tip 36 to form three suture paths P. Three sutures 70 are each wrapped a few times around the proximal end of an associated coil 76 of one of three coil members 74. The coil members 74 are then advanced along the paths P of the elongated member 15 through the hollow interiors of the first set of needles 30. The coil members 74 then travel out of the first set of needles 30 into associated needle lumen portions 38 in the tip 36 (FIG. 6).

The coil members 74 then traverse the U-shaped needle lumen portions 38 into the hollow interiors of the second set of needles 32, as shown in FIG. 7. The coil members 74 are then passed through the second set of needle members 32 out of the elongated member 15. Each of the sutures 70 is moved along an associated path P to extend around the wound 12 until both ends 71 of the suture 70 extend out of the elongated member 15. The sutures 70 are cut from their respective coil members 74.

Figure 8:
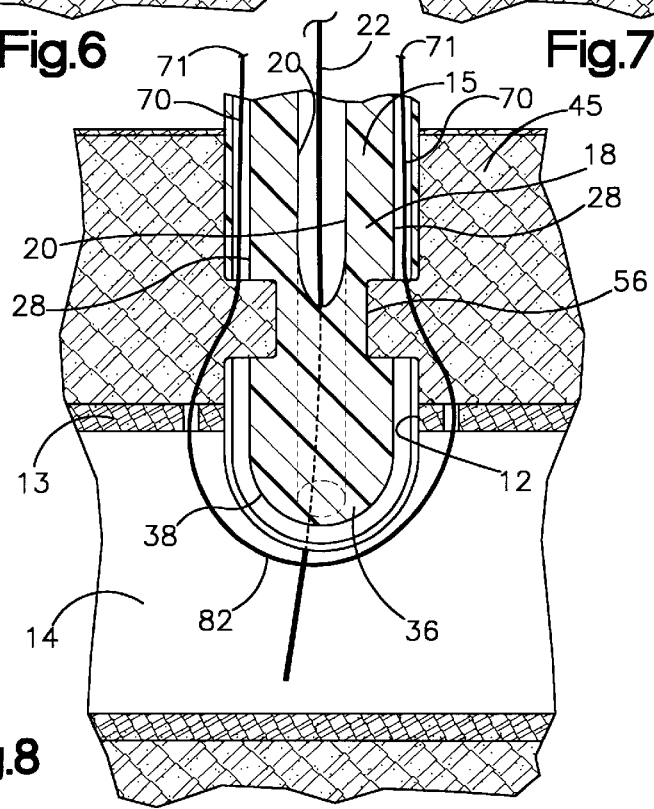
FIG. 8 is a cross-sectional view showing the suture delivery tool being withdrawn from the vessel and one of the sutures being removed from the tip.
Figure 9:
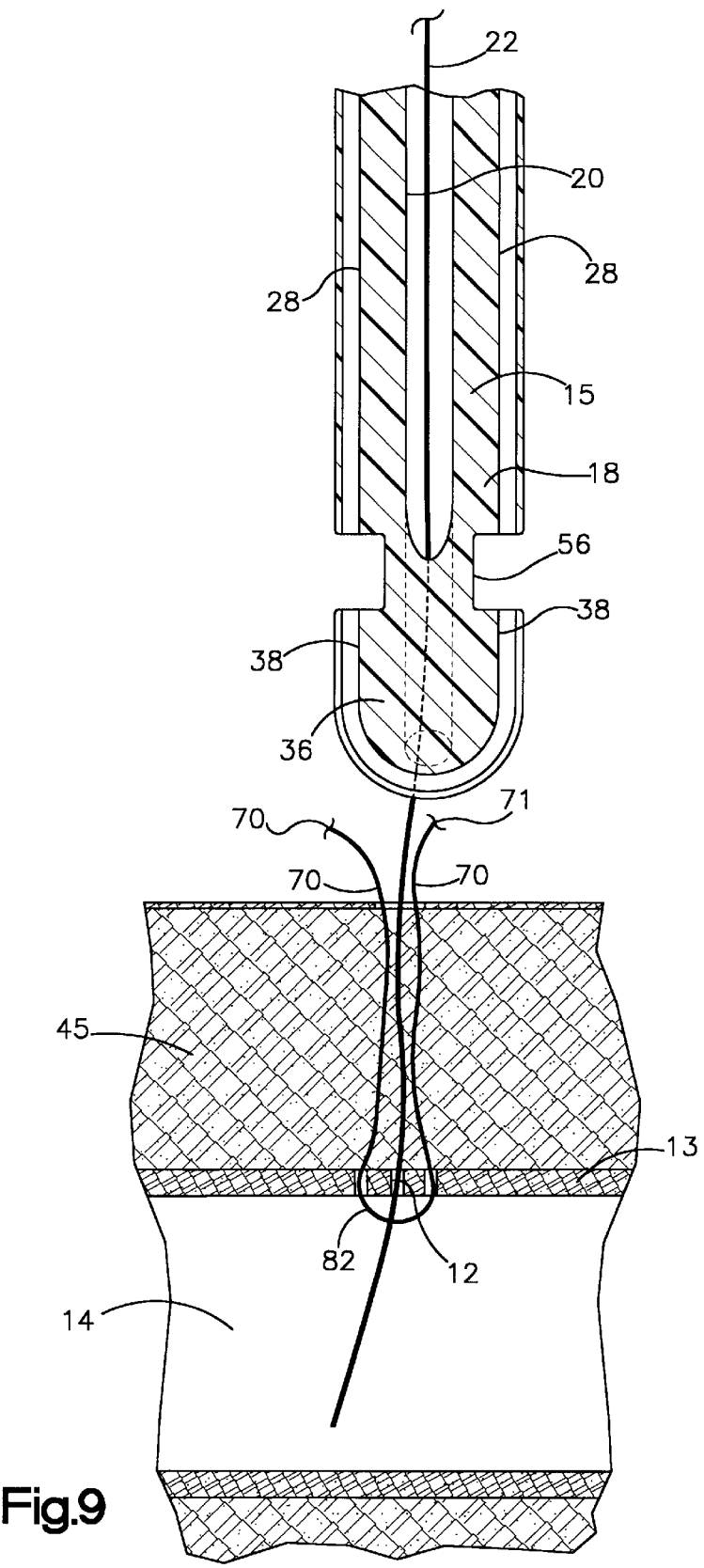
FIG. 9 is a cross-sectional view showing the suture delivery tool completely removed from the patient and a suture disposed on opposite sides of a wound in the vessel wall, with the guidewire still in place.

As shown in FIG. 8, the elongated member 15 is then removed from the vessel 14. In this process, lower loop portions 82 of the sutures 70 exit the tip 36 through the open second needle lumen portions 38. The outer opening of the needle lumen portions 38 is smaller than the size of the coil members 74 but larger than the size of the sutures 70. As shown in FIG. 9, the elongated member 15 is then completely removed from the patient's body, leaving the sutures 70 in place around the wound 12. The guidewire 22 is removed from the vessel 14. The sutures 70 are cut from the elongated member 15 and knots are made. A conventional knot driver is used to close the wound 12 in a manner known to those skilled in the art.

Although the invention has been described in its preferred form with a certain degree of particularity, it will be understood that the present disclosure of the preferred embodiments has been made only by way of example and that various changes may be resorted to without departing from the true spirit and scope of the invention as hereafter claimed.

What is claimed is:

1. An apparatus for closing a wound in a vessel wall of a patient, comprising
    an elongated member having a proximal end portion and a distal end portion spaced from the proximal end portion along a longitudinal axis and having a distal end face, first needle lumens extending in said elongated member between the proximal end portion and the distal end portion,
    a tip disposed near the distal end portion of said elongated member and including second needle lumen portions aligned with said first needle lumens, said tip being spaced apart from said distal end face of said elongated member along the longitudinal axis to form a recess between said tip and said distal end face for receiving the vessel wall,
    at least two locker needle lumens extending between the proximal end portion and the distal end portion each having an outlet opening at an exterior surface of said elongated member, and
    at least two locker needles each disposed in an associated one of said locker needle lumens and having a shape effective to penetrate tissue of the patient,
    wherein each said outlet opening is spaced a distance above said tip and each said locker needle lumen has a portion that extends to said outlet opening at an angle with respect to the longitudinal axis, said distance and said angle being effective to prevent said locker needle from contacting the vessel wall of the patient.

2. The apparatus of claim 1 wherein said second needle lumen portions are substantially U-shaped.

3. The apparatus of claim 1 wherein said second needle lumen portions communicate with an exterior surface of said tip along an entire length of said second needle lumen portions.

4. The apparatus of claim 1 wherein said first needle lumens are arcuately arranged around a central longitudinal axis in a plane extending perpendicular to the longitudinal direction.

5. The apparatus of claim 1 wherein each said angled locker needle lumen portion extends at an angle that is less than 90° with respect to a portion of the longitudinal axis above said locker needle lumen portion.

6. The apparatus of claim 5 wherein said angle ranges from 50 to 70°.

7. An apparatus for closing a wound in a vessel wall of a patient, comprising
    an elongated member having a proximal end portion and a distal end portion spaced from the proximal end portion along a longitudinal axis and having a distal end face, a central guidewire lumen extending between the proximal end portion and the distal end portion for receiving a guidewire, and first and second groups of at least three first needle lumens extending in said elongated member between the proximal end portion and the distal end portion,
    a tip disposed near the distal end portion of said elongated member and including second needle lumen portions aligned with said first needle lumens, said tip being spaced apart from said distal end face of said elongated member along the longitudinal axis to form a recess between said tip and said distal end face for receiving the vessel wall,
    first and second needle sets each having at least three hollow needle members, wherein said needle members and said second needle lumen portions cooperate to form suture paths,
    at least two locker needle lumens each extending between the proximal end portion and the distal end portion and having an outlet opening at an exterior surface of said elongated member, and
    at least two locker needles each disposed in an associated one of said locker needle lumens and having a shape effective to penetrate tissue of the patient,
    wherein each said outlet opening is spaced a distance above said tip and each said locker needle lumen has a portion that extends to said outlet opening at an angle with respect to the longitudinal axis, said distance and said angle being effective to prevent said locker needles from contacting the vessel wall of the patient.

8. The apparatus of claim 7 wherein said second needle lumen portions are substantially U-shaped.

9. The apparatus of claim 7 wherein each of said second needle lumen portions communicates with an exterior surface of said tip along an entire length of said second needle lumen portion.

10. The apparatus of claim 7 further comprising at least three members for advancing the sutures and at least three sutures which each can be connected to an associated one of the suture advancing members.

11. The apparatus of claim 7 wherein said elongated member and said tip have an oblong cross-sectional shape in a plane extending perpendicular to the longitudinal direction.

12. The apparatus of claim 7 wherein each said angled locker needle lumen portion extends at an angle that is less than 90° with respect to a portion of the longitudinal axis above said locker needle lumen portion.

13. A method for closing a wound in a vessel wall of a patient, comprising the steps of inserting a tip of an elongated member through a wound in a vessel wall of a patient and into the vessel, inserting locker needle members into locker needle lumens in the elongated member, each of said locker needle lumens having an outlet opening at an exterior surface of the elongated member, wherein each said outlet opening is spaced a distance above said tip and each said locker needle lumen has a portion that extends to said outlet opening at an angle with respect to a longitudinal axis along which the elongated member extends, inserting locker needles through the angled locker needle lumen portions, through the outlet openings and into tissue of the patient and preventing said locker needles from contacting the vessel wall, inserting at least one hollow needle member into at least one first needle lumen of the elongated member on one side of the wound and inserting at least one hollow needle member into at least one first needle lumen of the elongated member on another side of the wound, puncturing the vessel wall by moving the needle member on one side of the wound into a needle lumen portion in the tip, and by moving the needle member on the other side of the wound into the needle lumen portion, passing sutures through the needle members and the needle lumen portion, removing the elongated member from the wound, and closing the wound with the sutures.

14. The method of claim 13 further comprising introducing a guidewire into the wound and guiding the elongated member to the wound by sliding the elongated member over the guidewire.

15. The method of claim 13 further comprising removing the sutures from each second needle lumen portion of the tip while the sutures are disposed in the needle members.

16. The method of claim 13 further comprising positioning the vessel wall in the recess by inserting the elongated member into the vessel with only the first set of needle members disposed in the first needle lumens until blood flows from said first needle lumens without needle members, and withdrawing the elongated member to a position where the blood flow stops.

17. The method of claim 13 wherein each of the needle members is disposed a distance not greater than 1 mm from an edge of the wound.

18. A method for closing a wound in a vessel wall of a patient, comprising the steps of guiding a tip of an elongated member through a wound in a vessel wall of a patient and into the vessel by sliding the elongated member over a guidewire an a longitudinal axis along which the elongated member extends, the tip being spaced apart from a distal end face of the elongated member along the longitudinal axis to form a recess between the elongated member and the tip, inserting locker needle members into locker needle lumens in the elongated member, each of said locker needle lumens having an outlet opening at an exterior surface of the elongated member, wherein each said outlet opening is spaced a distance above said tip and each said locker needle lumen has a portion that extends to said outlet opening at an angle with respect to the longitudinal axis, inserting locker needles through the angled locker needle lumen portions, through the outlet openings and into tissue of the patient and preventing said locker needles from contacting the vessel wall, inserting a first set of at least three hollow needle members into a first group of needle lumens of the elongated member through the vessel wall on one side of the wound, inserting a second set of at least three hollow needle members into a second group of needle lumens of the elongated member through the vessel wall on another side of the wound, wherein said first and second groups of needle lumens are arcuately arranged around a central longitudinal axis of the elongated member in a plane extending perpendicular to the longitudinal direction, whereby after passing through said needle lumens said needle members form corresponding punctures arranged arcuately around the wound, wherein needle lumen portions are disposed in the tip in alignment with said needle lumens, and the needle members of the first and second sets are moved into said needle lumen portions in the tip, passing at least three sutures into the elongated member through the interior of the first set of hollow needle members, into the needle lumen portions in the tip, and out the elongated member through the interior of the second set of hollow needle members, removing the elongated member from the vessel, removing the guidewire from the vessel, and tying the sutures to close the wound.

\* \* \* \* \*